(12) United States Patent
Woo et al.

(10) Patent No.: US 7,019,132 B2
(45) Date of Patent: Mar. 28, 2006

(54) PORPHYRIN DERIVATIVES

(75) Inventors: Nam-Tae Woo, Seoul (KR); Min-Suk Kang, Ansan (KR); Won-Young Lee, Seoul (KR); Chang-Hee Lee, Chuncheon (KR); Yong-Rok Kim, Seoul (KR); Dai-Woon Lee, Sungnam (KR); Dong-Hoon Won, Wonju (KR); Si-Hwan Ko, Goyang (KR)

(73) Assignee: Kostarworld Co., Ltd., (KR)

( * ) Notice: Subject to any disclaimer, the term of this patent is extended or adjusted under 35 U.S.C. 154(b) by 0 days.

(21) Appl. No.: 10/718,734

(22) Filed: Nov. 20, 2003

(65) Prior Publication Data

US 2004/0142917 A1    Jul. 22, 2004

(30) Foreign Application Priority Data

Jan. 16, 2003  (KR) .................. 10-2003-0002921
Jan. 16, 2003  (KR) .................. 10-2003-0002922

(51) Int. Cl.
*C07B 47/00*   (2006.01)

(52) U.S. Cl. ............ 540/145; 534/15; 424/9.362; 424/9.61; 514/185; 514/410

(58) Field of Classification Search ........... 540/145; 534/15; 514/185, 410; 424/9.1
See application file for complete search history.

(56) References Cited

U.S. PATENT DOCUMENTS

| | | | |
|---|---|---|---|
| 4,882,234 | A | 11/1989 | Lai et al. |
| 5,587,394 | A | 12/1996 | Morgan et al. |
| 5,633,275 | A | 5/1997 | Mori et al. |
| 5,648,485 | A | 7/1997 | Dolphin et al. |
| 5,654,423 | A | 8/1997 | Kahl et al. |
| 5,675,001 | A | 10/1997 | Hoffman et al. |
| 5,693,632 | A | 12/1997 | Morgan et al. |
| 5,703,230 | A | 12/1997 | Boyle et al. |
| 5,705,622 | A | 1/1998 | McCapra |

FOREIGN PATENT DOCUMENTS

| | | |
|---|---|---|
| CA | 2121716 | 12/1994 |
| EP | 0569113 | 11/1993 |
| JP | 09-071531 | 3/1997 |

OTHER PUBLICATIONS

Hynninen et al. Tracing the Allomerization Pathways of Chlorophylls by )-Labeling and Mass Spectrometry., May 18, 2002., Journal of Organic Chemistry, 67 pp. 4055-4061.*

Wasielewski et al. Sythesis of Covalently Linked Dimeric Derivatives of Chlorophyl a, Pyrochlorophyll a, Chlorophyll a, and Bacteriochlorophyll a. 1980. Journal of Organic Chemistry, 45 pp. 1969-1974.*

Holt, A.S. The Phase Test Intermediate and the Allomerization of Chlorophyll a. 1958. Canadian Journal of Biochemistry and Physiology, 36 pp. 439-456.*

Katzung, Bertram. Basic and Clinical Pharmacology., Seventh Edition 1998. Appleton & Lange. pp 881-884.*

Hynninen et al. Tracing the Allomerization Pathways of Chlorophylls by )-Labeling and Mass Spectrometry., May 18, 2002., Journal of Organic Chemistry, 67 pp. 4055-4061.*

Wasielewski et al. Sythesis of Covalently Linked Dimeric Derivatives of Chlorophyl a, Pyrochlorophyll a, Chlorophyll a, and Bacteriochlorophyll a. 1980. Journal of Organic Chemistry, 45 pp. 1969-1974.*

Holt, A.S. The Phase Test Intermediate and the Allomerization of Chlorophyll a. 1958. Canadian Journal of Biochemistry and Physiology, 36 pp. 439-456.*

* cited by examiner

*Primary Examiner*—James O. Wilson
*Assistant Examiner*—Matthew L. Fedowitz
(74) *Attorney, Agent, or Firm*—Anderson Kill & Olick, PC

(57) ABSTRACT

The present invention is related to novel photopyrin compounds and the pharmaceutically acceptable salt thereof useful as an anticancer or photodynamic diagnostic agent by way of reproducing singlet state oxygen radical and the inventive compounds have superior advantages such as excellent photon yield to produce singlet oxygen, good physical stability and potent cell cytotoxicity to conventional photosensitizer. The present invention also provides a pharmaceutical composition comprising a novel photopyrin compound of formula (I) to (VII) or a pharmaceutically acceptable salt thereof as an active ingredient for preventing or treating various cancers such as stomach cancer, liver cancer, lung cancer, cervical cancer and breast cancer in human or mammal together with a pharmaceutically acceptable carrier.

3 Claims, 10 Drawing Sheets

1) 666.0 nm
2) 609.0 nm
3) 557.0 nm
4) 536.0 nm
5) 507.0 nm
6) 472.5 nm

PORPHYRIN DERIVATIVES

CROSS REFERENCE TO RELATED APPLICATION

This application is an international patent application, claiming the benefit under 35 USC § 111(a) of Korean Patent Application No. 10-03-2921, 2922, filed Jan. 16, 2003.

FIELD OF THE INVENTION

The present invention relates to porphyrin derivatives or the pharmaceutically acceptable salts thereof and pharmaceutical compositions comprising the same useful to photodynamic therapy.

BACKGROUND

Photodynamic therapy (PDT) is one of therapeutic techniques to treat incurable diseases using by photosensitizer drugs having a selectivity and photoenhancing activity to cancer cells or various tumors without a surgical operation and complication occurring in chemotherapy.

The action mechanism of photosensitizer drugs is that for example, the drug is intravenously administrated to a patient and the optimum amount of light is irradiated thereto to form excited state of photosensitizer. The drugs give rise to activating oxygen molecule to transform to be excited singlet oxygen state, new radical or new chemical species resulting in attacking and demolishing cancer cells or various tumor cells selectively.

Representative photosensitizers are porphyrin compounds which have been extracted from silk worm feces or mulberry leaf or green algae and have appropriate spectrophotometric characteristics to be used as photosensitizers. Their most important characteristics are to give rise to electron transition due to infrared light whose wavelength from 700 to 900 nm allowing relative great cell penetrating activity and the production of excited state of triplet oxygen thereby.

Porphyrin derivatives as photosensitizers can selectively not only penetrate or be accumulated in tumor site but also emit fluorescence or phosphorescence and therefore, can be useful as an early stage diagnostic tool.

There have been lots of reports on several porphyrin derivatives in prior art. For example, U.S. Pat. Nos. 5,633,275; 5,654,423; 5,675,001; 5,703,230; 5,705,622 and U.S. Pat. No. 4,882,234 disclose several photofrin II compounds. It has been reported that one of those is on sale and some of those are on clinical trials now, however, those porphyrin II are the mixtures consisting of several oligomers ether-linked with haematoporphyrin (HpD).

PCT/WO 97/29915 (A) discloses BPDMA (verteporphin), a benzoporphyrin derivative, known to show specific effect on skin cancer, psoriasis and AMD. M-THPC disclosed in PCT/WO97/48393 and known to be useful in treating trachea and lung cancer or Monoaspitylchlorine disclosed in CA Registration No. 2121716 and Japanese Patent Registration No. 09071531 and known to be useful to photodynamic therapy as one of chlorine derivatives have been reported together with related several patents i.e., PCT/WO97/19081, PCT/WO 97/32885; EP 569113; U.S. Pat. Nos. 5,587,394; 5,648,485 and 5,693,632; all of which are incorporated herein by reference.

However, most of those porphyrin group compounds are meso-tetraphenylporphyrin derivatives, chlorine group, chlorophyll group, purpurine group, nerdine, Diels-Elder Reaction Adducts and so on and 5-aminolevulanic acid, phthalocyanin and the like as non-porphyrin group compounds.

Since the yield of producing singlet oxygen molecule is correlated with cell cytotoxic activity directly, the yield is in proportion with cell cytotoxic activity, which is most crucial factor together with the retention time in human body in photodynamic therapy and remains to be improved till now. However, above described clinically using porphyrin compounds as photosensitizer drugs have been reported to have several disadvantages such as too long retention time in human body delivering unfavorable photo-toxicity, which remains to be improved till now.

Accordingly, present inventors have endeavored to find novel porphyrin derivatives or their pharmaceutically acceptable salt thereof which has newly modified chlorine group improved the disadvantage of conventional photosensitizer drug i.e., physical stability, superior yield to reproduce singlet state oxygen radical and superior cell cytotoxic activity to conventional porphyrin derivatives and finally accomplished the present invention.

SUMMARY OF THE INVENTION

Present invention provides novel porphyrin compounds and the pharmaceutically acceptable salts thereof useful as a photosensitizer in photodynamic therapy.

Present invention also provides pharmaceutical compositions comprising the above described porphyrin compounds as an active ingredient in an amount effective to treat or prevent cancer disease, together with a pharmaceutically acceptable carrier.

Present invention also provides a use of above described porphyrin compounds for the preparation for manufacture of medicament employed for treating or preventing various cancer in human or mammal.

Present invention also provides a method of treating or preventing cancer in a mammal wherein the method comprises administering a therapeutically effective amount of above described compound or pharmaceutically acceptable salts thereof.

BRIEF DESCRIPTION OF THE DRAWINGS

The above and other objects, features and other advantages of the present invention will more clearly understood from the following detailed description taken in conjunction with the accompanying drawings, in which.

DETAILED DESCRIPTION OF THE INVENTION

Figure 1:
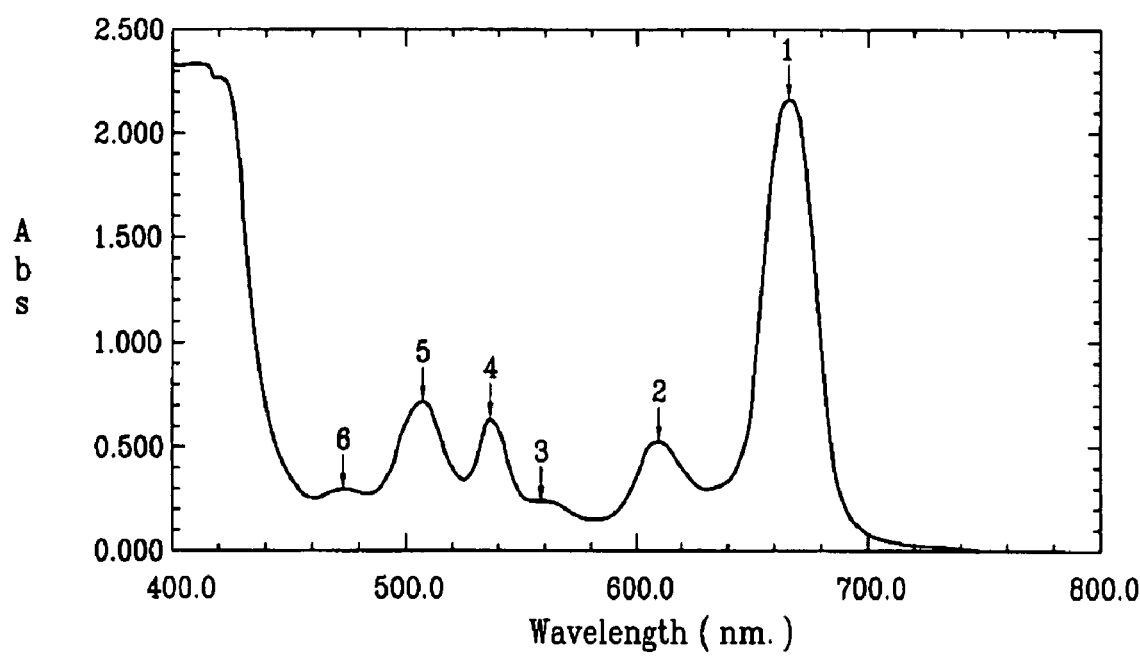
FIG. 1 shows UV spectrum of present photosensitizing substance (DH-1-180-3)

Thus, it is an object to provide novel compound represented by the following formula (I), and the pharmaceutically acceptable salt thereof:

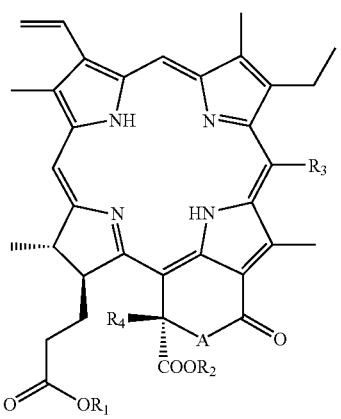

(I)

wherein $R_1$, $R_2$ is independently a straight or branched lower alkyl or alkoxy group having 1 to 6 carbon atoms, a polyethyleneglycol group or a sulfonyl group;

$R_3$ is a hydrogen atom, an alkoxy group having 1 to 6 carbon atoms or a polyethyleneglycol group;

$R_4$ is a hydrogen atom, a hydroxyl group or an alkoxy group having 1 to 6 carbon atom, A is linked directly or bridged with oxygen atom, which may be chelating with transition metal ion comprising Ni metal ion.

A preferred embodiment comprises the compounds of the formula (I) where $R_1$, $R_2$ is selected from the group consisting of an ethyl group, a propyl group, an ethyleneglycol group, diethyleneglycol group, triethyleneglycol group, tetraethyleneglycol group, hexaethyleneglycol group, heptaethyleneglycol group or a methoxyethyleneglycol group; $R_3$ is selected from the group consisting of a hydrogen atom, an ethyl group, a propyl group, a methoxy, an ethoxy group, an ethyleneglycol group, triethyleneglycol group, hexaethylene group; $R_4$ is a hydrogen atom, a hydroxyl group or an methoxy group; and A is linked directly providing that $R_1$ and $R_2$ is the same group and $R_2$ is different from $R_1$ or $R_3$.

Exemplary preferable compound of the present invention comprises following compounds represented by general formula (II) to (VII).

Accordingly, it is a further object to provide novel compound represented by the following formula (II), and the pharmaceutically acceptable salt thereof:

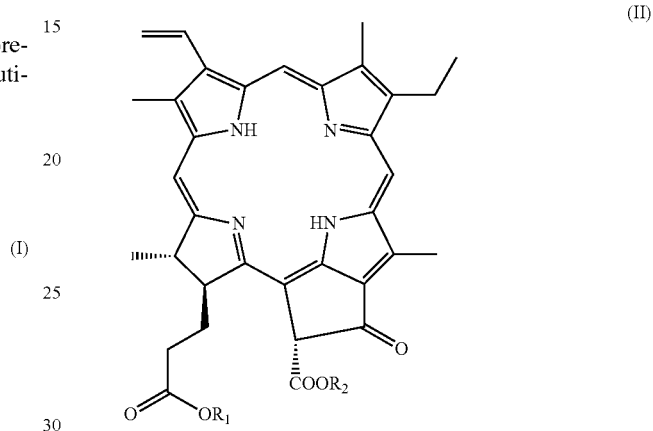

(II)

wherein $R_1$, $R_2$ is independently a straight or branched lower alkyl or alkoxy group having 1 to 6 carbon atoms, a polyethyleneglycol group or a sulfonyl group, which may be chelating with transition metal ion comprising Ni metal ion.

Accordingly, it is a still further object to provide novel compound represented by the following general formula (III), and the pharmaceutically acceptable salt thereof:

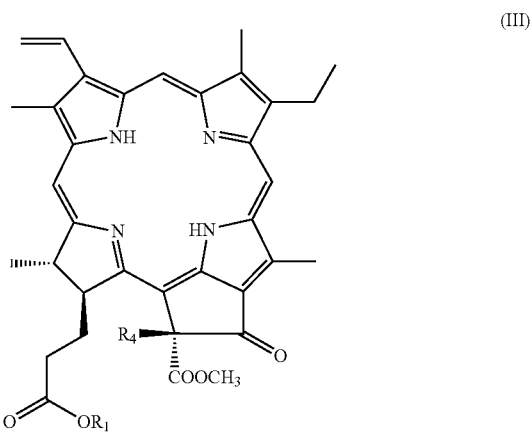

(III)

wherein $R_1$ is a polyethyleneglycol group;

$R_4$ is a hydrogen atom or a hydroxyl group.

Accordingly, it is a still further object to provide novel compound represented by the following general formula (IV), and the pharmaceutically acceptable salt thereof:

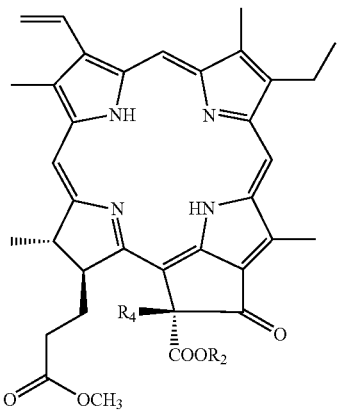

(IV)

wherein
$R_2$ is a bromopropyl group, or a polyethyleneglycol group;
$R_4$ is a hydrogen atom or a hydroxyl group.

Accordingly, it is a still further object to provide novel compound represented by the following general formula (V), the pharmaceutically acceptable salt thereof:

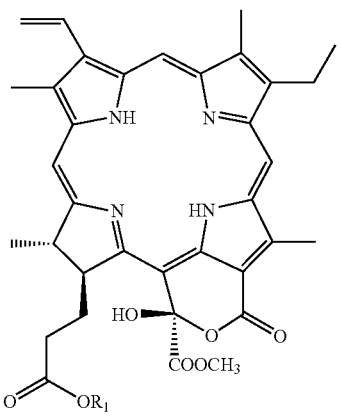

(V)

wherein
$R_1$ is a methyl, ethyl group, or an ethyleneglycol group.

It is a still further object to provide novel compound represented by the following general formula (VI), the pharmaceutically acceptable salt thereof:

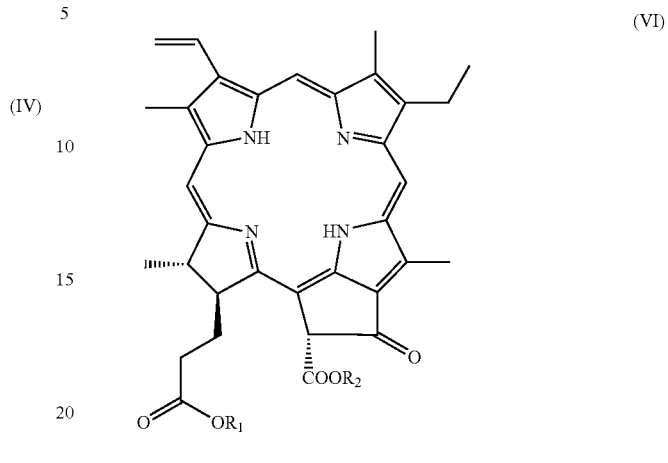

(VI)

wherein
$R_1$, $R_2$ is independently a polyethyleneglycol group.

It is a still further object to provide novel compound represented by the following chemical formula (VII), the pharmaceutically acceptable salt thereof:

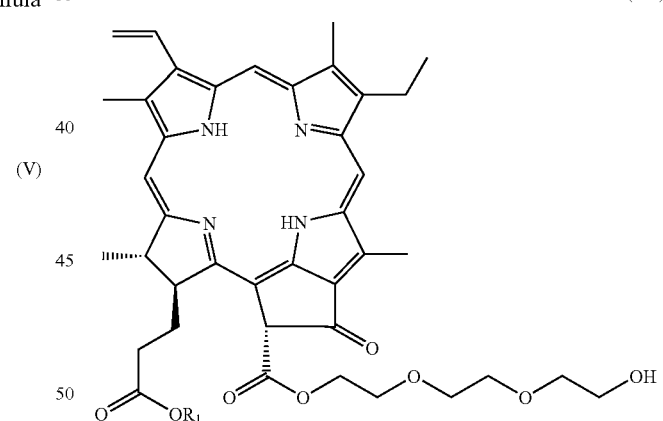

(VII)

wherein
$R_1$ is a polyethyleneglycol group.

The inventive compounds represented by general formula (I) to (VII) can be transformed into their pharmaceutically acceptable salt by the conventional method well known in the art. For example, the acid-addition salt formed by a pharmaceutically acceptable free acid thereof is useful and can be prepared by the conventional method, for example, after dissolving the compound in the excess amount of acid solution, the salts are precipitated by the water-miscible organic solvent such as methanol, ethanol, acetone or acetonitrile to prepare acid addition salt and further the mixture of equivalent amount of compound and diluted acid with water or alcohol such as glycol monomethylether, may be heated and subsequently dried by evaporation or filtrated under reduced pressure to obtain dried salt.

As a free acid of above-described method, organic acid or inorganic acid can be used. For example, organic acid such as methansulfonic acid, p-toluensulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compounds may be prepared using by base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the compound represented by general formula (I) to (VII) comprise all the acidic or basic salt which can be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate(mesylate) salt and p-toluenesulfonate (tosylate) salt etc, which can be prepared by the conventional method well known in the art.

There may exist in the form of optically different diastereomers since the compounds represented by general formula (I) to (VII) have unsymmetrical centers, accordingly, the compounds of the present invention comprise all the optically active isomers, R or S stereoisomers and the mixtures thereof. Present invention also comprises all the uses of racemic mixture, more than one optically active isomer or the mixtures thereof as well as all the preparation or isolation method of the diastereomer well known in the art.

The compounds of the present invention may be chemically synthesized by the methods in the reaction schemes hereinafter, which are merely exemplary and in no way limit the invention. The reaction schemes show the steps for preparing the representative compounds of the present invention, and other compounds also may be produced by following the steps with appropriate modifications of reagents and starting materials, which are envisaged by those skilled in the art.

GENERAL SYNTHETIC PROCEDURES

For example, the porphyrin compounds represented by general formula (I) the pharmaceutically acceptable salt thereof may be prepared by the following steps: pheophytin α or 10-hydroxypheophytin α is obtained by extracting dried silk worm feces or green algae with water or organic solvent such as alcohol, acetone or chloroform etc to obtain porphyrin containing extract; and the extract is subjected to repeated column chromatography and Thin layer chromatography to isolate pheophytin α (1) or 10-hydroxypheophytin α; and then the isolated compound is reacted with alcohol ($R_1OH$) in the presence of acid or base at room temperature or reflux condition to obtain pheophorbide α alkylester (2) or 10-hydroxy pheophorbide α methylester which is used as starting material for the preparation of the compounds represented by formula (II) to (VII).

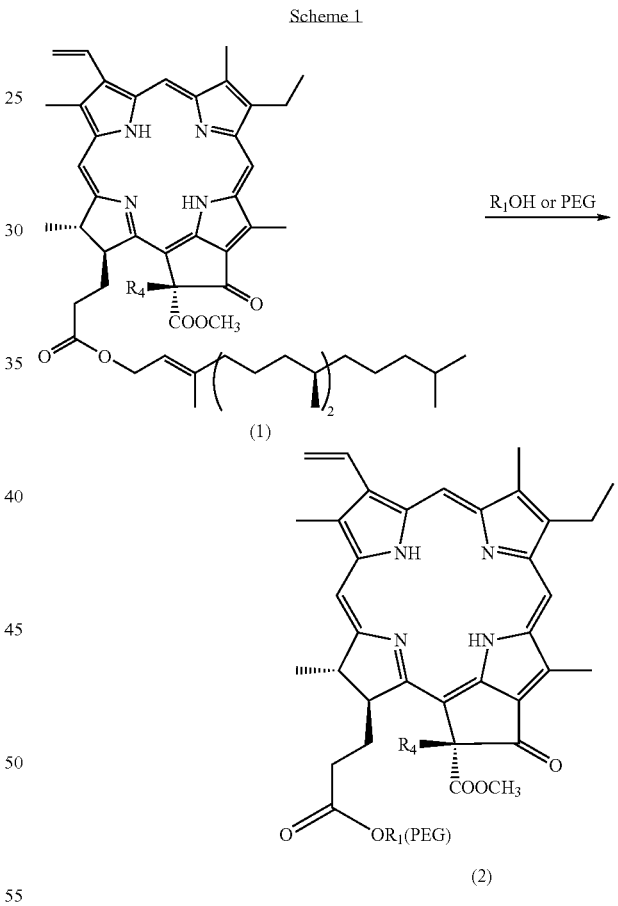

As depicted in above Scheme 1, pheophytin α (1) is reacted with conventional alcohol ($R_1OH$) such as 3-bromo-1-propanol or PEG such as ethylenglycol, triethyleneglycol, in the presence of acid preferably, sulfuric acid at nitrogen gas atmosphere in solvent such as toluene, oxazine, dichloromethane for 1 hr to 3 days, preferably 24 hrs, washed with appropriate washing solution and then remaining solvent is removed by evaporator in vacuo to obtain pheophorbide α ester (2) as a final product, which is further purified and isolated with column chromatography or TLC well-known in the art.

Detailed procedure described in scheme 1 will be explained in Example 1 to 3 herein.

Detailed procedure described in scheme 2 will be explained in Example 4 to 5 herein.

Scheme 2

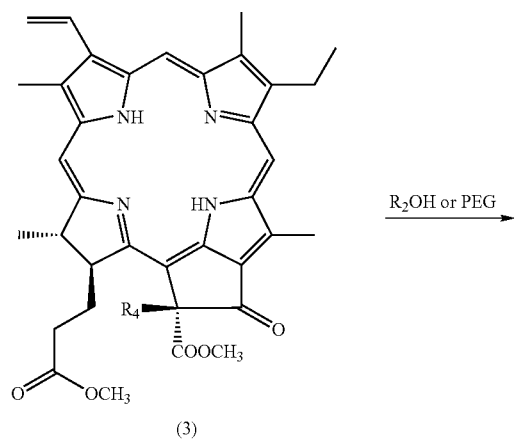

(3)

R₂OH or PEG →

Scheme 3

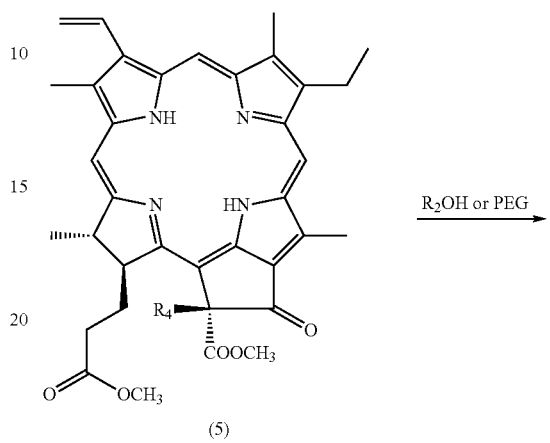

(5)

R₂OH or PEG →

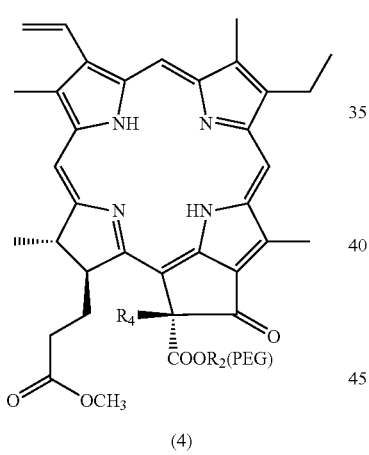

(4)

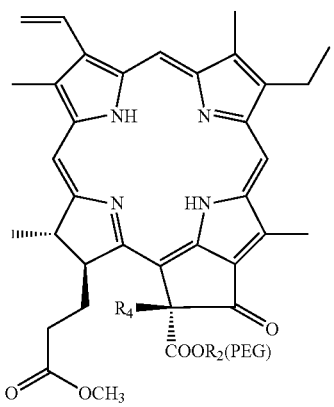

(6)

As depicted in above Scheme 2, methyl pheophorbide α methyl ester (3) is reacted with alcohol (R₂OH) such as 3-bromo-1-propanol or PEG such as ethylenglycol, triethyleneglycol, in the presence of acid preferably, sulfuric acid or base preferably, pyridine, at nitrogen gas atmosphere in inert solvent such as toluene, oxazine, dichloromethane for 1 hr to 3 days, preferably 24 hrs, washed with appropriate washing solution and remaining solvent is removed by evaporator in vacuo to obtain pheophorbide α methylester, final product (4), which is further purified and isolated with column chromatography or TLC well-known in the art.

As depicted in above Scheme 3, methyl pheophorbide α methyl ester (5) is reacted with oxazine in the presence of base preferably, pyridine, at nitrogen gas atmosphere in inert solvent such as toluene, oxazine, dichloromethane for 1 hr to 3 days, preferably 24 hrs, washed with appropriate washing solution such as ammonium sulfate and then remaining solvent is removed by evaporator in vacuo to obtain oxazine type pheophorbide α methylester, final product (6) which is further purified and isolated with column chromatography or TLC well-known in the art.

Detailed procedure described in scheme 3 will be explained in Example 6 herein.

Scheme 4

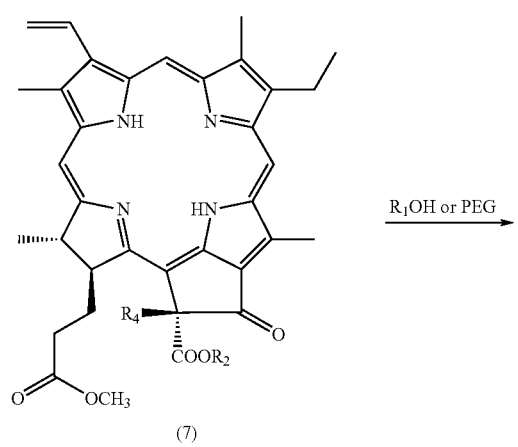

(7)

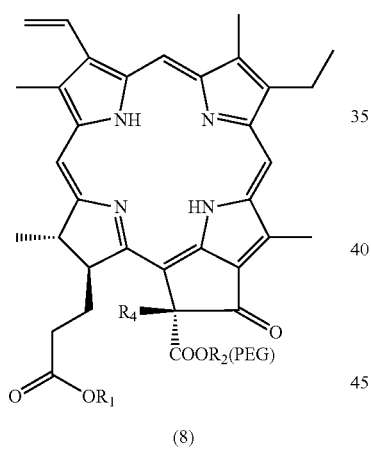

(8)

Scheme 5

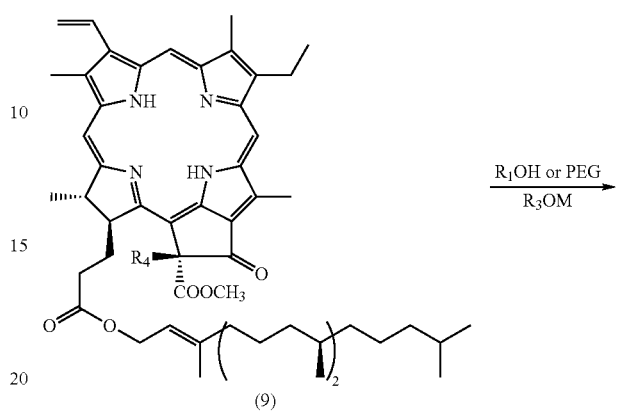

(9)

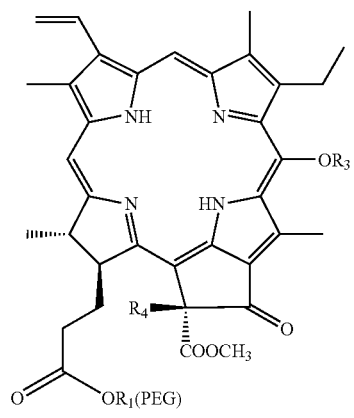

(10)

As depicted in above Scheme 4, methyl pheophorbide α methyl ester (7) is reacted with triethyleneglycol in the presence of acid preferably, sulfuric acid, at nitrogen gas atmosphere in inert solvent such as toluene, oxazine, dichloromethane for 1 hr to 3 days, preferably 24 hrs, washed with appropriate washing solution such as sodium bicarbonate and remaining solvent is removed by evaporator in vacuo to obtain pheophorbide α methylester, final product (8), which is further purified and isolated with column chromatography or TLC well-known in the art.

Detailed procedure described in scheme 4 will be explained in Example 7 and 8 herein.

As depicted in above Scheme 5, pheophytin α (9) is reacted with conventional alcohol ($R_1OH$) such as 3-bromo-1-propanol or PEG such as ethylenglycol, triethyleneglycol, in the presence of acid preferably, sulfuric acid at nitrogen gas atmosphere in solvent such as toluene, oxazine, dichloromethane for 1 hr to 3 days, preferably 24 hrs, washed with appropriate washing solution and remaining solvent is removed by evaporator in vacuo. The compound is further subjected to oxidation with oxidizing agent such as $KMnO_4$, $NaIO_4$, in the presence of under basic condition at nitrogen gas atmosphere in protic solvents such as water to obtain pheophorbide α alcohol as a final product (10), which is further purified and isolated with column chromatography or TLC well-known in the art.

Detailed procedure described in scheme 5 will be explained in Example 9 herein.

The present invention also provides a pharmaceutical composition comprising a compound of formula (I) to (VII) or a pharmaceutically acceptable salt thereof as an active ingredient for preventing or treating various cancers such as stomach cancer, liver cancer, lung cancer, cervical cancer and breast cancer in human or mammal.

The compound of formula (I) to (VII) according to the present invention can be provided as a pharmaceutical composition containing pharmaceutically acceptable carriers, adjuvants or diluents. For example, the compounds of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

The compound of the present invention has potent anticancer activity and therefore, the pharmaceutical composition of the present invention thus may be employed to treat or prevent various cancer by way of reproducing singlet state oxygen radical and superior cell cytotoxic activity.

The present invention also provides an use of compound selected from the group consisting of compounds of formula (I) to (VII) or pharmaceutical acceptable salts thereof as a photosensitizer in photodynamic therapy.

In accordance with another aspect of the present invention, there is also provided an use of the compound (I) to (VII) for manufacture of medicament employed for treating or preventing various cancer such as stomach cancer, liver cancer, lung cancer, cervical cancer and breast cancer in human or mammal.

In accordance with another aspect of the present invention, there is also provided a method of treating or preventing various cancer such as stomach cancer, liver cancer, lung cancer, cervical cancer and breast cancer in human or mammal, wherein the method comprises administering a therapeutically effective amount of the compound of formula of (I) to (VII) or pharmaceutically acceptable salt thereof.

Hereinafter, the following formulation methods and excipients are merely exemplary and in no way limit the invention.

The compounds of the present invention in pharmaceutical dosage forms may be used in the form of their pharmaceutically acceptable salt, and also may be used alone or in appropriate association, as well as in combination with other pharmaceutically active compounds.

The compounds of the present invention may be formulated into preparations for injections by dissolving, suspending, or emulsifying them in aqueous solvents such as normal saline, 5% Dextrose, or non-aqueous solvent such as vegetable oil, synthetic aliphatic acid glycerides, esters of higher aliphatic acids or propylene glycol. The formulation may include conventional additives such as solubilizers, isotonic agents, suspending agents, emulsifying agents, stabilizers and preservatives.

The desirable dose of the inventive compounds varies depending on the condition and the weight of the subject, severity, drug form, route and period of administration, and may be chosen by those skilled in the art. However, in order to obtain desirable effects, it is generally recommended to administer at the amount ranging 0.0001–100 mg/kg, preferably 0.001–100 mg/kg by weight/day of the inventive compounds of the present invention. The dose may be administered in single or divided into several times per day. In terms of composition, the compounds should be present between 0.0001 to 10% by weight, preferably 0.0001 to 1% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intrathecal, epidural or intracerebroventricular injection.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

Example 1

Preparation of (13-diethylene glycol-oxycarbonyl)-pheophorbide α, methyl ester (2)

A solution of phephytin α (60 mg) in dichloromethane (3 ml) was poured in 50 ml of flask and treated with diethyleneglycol (20 ml) with stirring. 1 ml of sulfuric acid was added thereto, stirred for 3 hrs and then sodium bicarbonate water solution was added thereto. The solution was extracted with chloroform and the collected chloroform layer was concentrated by removing organic solvent. Remaining residue was purified by column chromatography to isolate 39 mg of (13-diethylene glycol-oxycarbonyl)-pheophorbide α methyl ester (2):

$^1$H-NMR (500 MHz, CDCl$_3$) δ: 9.51 (s, 1 H, meso-H), 9.37 (s, 1H, meso-H), 8.56 (s, 1H, meso-H), 7.99 (dd, 1H, J=6.2, 11.6 Hz, CH$_2$=CH), 6.29 (d, 1 H, J=17.8 Hz, CH$_2$=CH ), 6.28 (s. 1H, CH), 6.18 (d, 1H, J=11.6 Hz CH$_2$=CH), 4.48–4.41 (m, 1H, CH), 4.24–4.22 (m. 1H. CH), 4.19–4.04 (m, 2H, OCH$_2$), 3.87 (s, 3H, OCH$_3$), 3.71–366 (m, 2H, CH$_2$), 3.68 (s, 3H, CH$_3$), 3.64–3.42 (m, 6H, CH$_2$OCH$_2$CH$_2$), 3.40 (s,3H, CH$_3$), 3.22 (s, 3H, CH$_3$), 2.68–2.15 (m, 4H, CH$_2$CH$_2$), 1.82 (d, 3H, J=7.3 Hz, CH$_3$), 169 (t, 3H, J=7.6 Hz, CH$_3$), 0.56 (br. S., 1H, N—H), −1.61 (br. s., 1H, N—H).

Example 2

Preparation of (13-methoxytriethylene glycol-oxycarbonyl) pheophorbide α methyl ester (3)

29 mg of (13-methoxytriethylene glycol-oxycarbonyl) pheophorbide α methyl ester (3) was prepared by the same procedure with that described in above Example 1 except using phephytin (60 mg) and methoxytriethyleneglycol (30 ml):

$^1$H-NMR (500 MHz, CDCl$_3$) δ: 9.45 (s, 1 H, meso-H), 9.30 (s, 1H, meso-H), 8.55 (s, 1H, meso-H), 7.93 (dd, 1H, J=6.2, 11.5 Hz, CH$_2$=CH), 6.26 (s. 1H, CH), 6.25 (d, 1H, J=17.8 Hz CH=CH$_2$), 6.14 (d, 1H, J=11.3 Hz CH=CH$_2$), 4.49–4.44 (m, 1H, CH), 4.22–4.20 (m. 1H. CH), 4.15–4.02

(m, 2H, OCH$_2$), 3.88 (s, 3H, OCH$_3$), 3.67 (s, 3H, CH$_3$), 3.60 (q, 2H, CH$_3$—CH$_2$), 3.51–3.45 (m, 8H, CH$_2$ OCH$_2$ CH$_2$ OCH$_2$), 3.41–3.37 (m, 2H, CH$_2$), 3.38 (s, 3H, CH$_3$), 3.25 (s, 3H, OCH$_3$), 3.16 (s, 3H, CH$_3$), 2.65–2.18 (m, 4H, CH$_2$CH$_2$), 1.82 (d, 3H, J=7.2 Hz, CH$_3$), 1.68–1.64 (m, 3H, CH$_3$), 0.51 (br.s., 1H, N—H), −1.61 (br. s., 1H, N—H).

Example 3

Preparation of 13-hydroxy-(13-methoxytriethylene glycoloxy carbonyl) pheophorbide α methyl ester (4)

22 mg of 13-hydroxy-(13-methoxytriethylene glycoloxy carbonyl) pheophorbide α methyl ester (4) was prepared by the same procedure with that described in above Example 1 except using 10-hydroxyphephytin α (60 mg) and methoxytriethyleneglycol (20 ml):

$^1$H-NMR (500 MHz, CDCl$_3$) δ: 9.62 (s, 1 H, meso-H), 9.49 (s, 1H, meso-H), 8.65 (s, 1H, meso-H), 8.03 (dd, 1H, J=6.3, 11.4 Hz, CH$_2$=CH), 6.31 (d, 1H, J=17.8 Hz, CH=CH$_2$), 6.20 (d, 1H, J=11.6 Hz, CH=CH$_2$), 5.78 (s, 1H, OH), 4.52–4.47 (m, 1H, CH), 4.30–4.14 (m, 3H, CH and OCH$_2$), 3.74 (s, 3H, OCH$_3$), 3.74–3.70 (m, 2H, CH$_2$ ), 3.63–3.57 (m, 8H, CH$_2$OCH$_2$CH$_2$OCH$_2$), 3.60 (s, 3H, CH$_3$), 3.47–3.46 (m, 2H, CH$_2$), 3.43 (s 3H, CH$_3$), 3.29 (s, 3H, CH$_3$), 3.27 (s, 3H, OCH$_3$), 3.02–2.95, 2.64–2.57 and 2.35–2.21 (m, 4H, CH$_2$CH$_2$), 1.71 (t, 3H, J=7.5 Hz, CH$_3$), 1.60 (d, 3H, J=7.1 Hz, CH$_3$), 0.30 (br. s., 1H, N—H), −1.83 (br. s., 1H, N—H).

Example 4

Preparation of [13-(3-bromo-1-propyloxycarbonyl)]-pheophorbide α methy ester (5)

A solution of methyl pheophorbide α methyl ester (4) (20 mg) in pyridine (4 ml) and toluene (8 ml), was poured in 50 ml of flask and treated with 3-bromo-1-propanol (0.003 ml) with stirring and heated for 5 hrs. And then the solution was washed with ammonium chloride water solution and extracted with methylene chloride. The collected methylene chloride layer was concentrated by removing organic solvent and remaining residue was purified by column chromatography to isolate 11 mg of [13-(3-bromo-1-propyloxycarbonyl)]-pheophorbide α methy ester (5):

$^1$H-NMR (500 MHz, CDCl$_3$) δ: 9.52 (s, 1 H, meso-H), 9.38 (s, 1H, meso-H), 8.56 (s, 1H, meso-H), 7.99 (dd, 1H, J=6.2, 11.7 Hz, CH$_2$=CH), 6.28 (d, 1H, J=19.3 Hz, CH=CH$_2$), 6.26 (d, 1H, CH), J=11.6 Hz, CH=CH$_2$), 6.18 (d, 1H, J=11.6 Hz, CH=CH$_2$), 4.52–4.45 (m, 3H, CH and OCH$_2$), 4.24–4.22 (m, 1H, CH), 3.68 (s, 3H, CH$_3$), 3.67 (m, 2H, CH$_2$), 3.56 (s, 3H, OCH$_3$), 3.47–3.34 (m, 2H, CH$_2$), 3.40 (s, 3H, CH$_3$), 3.23 (s, 3H, CH$_3$), 2.68–2.17 (m, 6H, CH$_2$CH$_2$ and CH$_2$), 1.83 (d, 3H, j=7.3Hz, CH$_3$), 1.69 (t, 3H, J=7.6 Hz, CH$_2$—CH$_3$), 0.54 (br. s., 1H, N—H), −1.62 (br. s., 1H, N—H).

Example 5

Preparation of (13-triethylene glycoloxy carbonyl)pheophorbide α methy ester (6)

In similar method in Example 4, A solution of methyl pheophorbide α methyl ester (4) (100 mg) in pyridine (16 ml) and toluene (15 ml), was poured in 50 ml of flask and treated with triethyleneglycol (0.033 ml) at nitrogen gas atmosphere and heated for 16 hrs. And then the solution was washed with ammonium chloride water solution and extracted with methylene chloride. The collected methylene chloride layer was concentrated by removing organic solvent and remaining residue was purified by column chromatography to isolate 73 mg of (13-triethylene glycoloxy carbonyl)pheophorbide α methy ester (6):

$^1$H-NMR (500 MHz, CDCl$_3$) δ: 9.53 (s, 1 H, meso-H), 9.40 (s, 1H, meso-H), 8.57 (s, 1H, meso-H), 8.00 (dd, 1H, J=6.3, 11.5 Hz, CH$_2$=CH), 6.30 (d, 1H, J=18.1 Hz, CH=CH$_2$), 6.27 (s, 1H, CH), 6.19 (d, 1H, J=6.3, 12.8 Hz, CH=CH$_2$), 4.49–4.45 (m,3H, CH and OCH$_2$), 4.26–4.24 (m, 1H, CH), 3.72–3.66 (m, 4H, CH$_2$ and OCH$_2$), 3.69 (s, 3H, CH$_3$), 3.55 (s, 3H, OCH$_3$), 3.49–3.39 (m, 4H, CH$_2$ OCH$_2$), 3.41 (s, 3H, CH$_3$), 3.31 (t, 2H, J=4.6 Hz, CH$_2$), 3.26–3.23 (m, 5H, CH$_2$ and CH$_3$), 2.66–2.21 (m, 5H, CH$_2$CH$_2$ and OH), 1.82 (d, 3H, J=7.3 Hz, CH$_3$), 1.70 (t, 3H, J=7.6 Hz, CH$_3$), 0.54 (br. s., 1H, N—H), −1.62 (br. s., 1H, N—H).

Example 6

Preparation of [13-hydroxy-(13-triethylene glycoloxy carbonyl)]-pheophorbide a methyl ester (7)

A solution of methyl pheophorbide α methyl ester (4) (50 mg) in pyridine (8 ml) and oxazine (23 ml), was dissolved in 10 ml of toluene and heated for 5 hrs. And then the solution was washed with ammonium chloride water solution and extracted with methylene chloride. The collected methylene chloride layer was concentrated by removing organic solvent and remaining residue was purified by column chromatography to isolate 21 mg of [13-hydroxy-(13-triethylene glycoloxy carbonyl)]-pheophorbide α methyl ester (7):

$^1$H-NMR (500 MHz, CDCl$_3$) δ: 9.76 (s, 1 H, meso-H), 9.54 (s, 1H, meso-H), 8.71 (s, 1H, meso-H), 8.01 (dd, 1H, J=6.2, 11.6 Hz, CH$_2$=CH), 6.34 (d, 1H, J=17.9 Hz, CH=CH$_2$), 6.18 (d, 1H, J=11.6 Hz, CH=CH$_2$), 6.09 (s, 1H, OH), 4.47–4.42 (m, 1H, CH), 4.07–4.05 (m, 1H, CH), 3.90 (s, 3H, OCH$_3$), 3.77 (s, 3H, OCH$_3$), 3.74(q, 2H, CH$_3$–CH$_2$), 3.54 (s, 3H, OCH$_3$), 3.44 (s, 3H, CH$_3$), 3.26 (s, 3H, CH$_3$), 2.61–1.78 (m, 4H, CH$_2$CH$_2$), 1.71 (t, 3H, J=7.6 Hz, CH$_2$—CH$_3$), 1.60 (d, 3H, J=7.1 Hz, CH$_3$), −1.09 (br. s., 1H, N—H), −1.41 (br. s., 1H, N—H).

Example 7

Preparation of Pheophorbide a Triethylene Glycol Methyl Ester (8)

A solution of methyl pheophorbide α methyl ester (30 mg) was dissolved in 20 ml of triethyleneglycol and stirred with adding 1 ml of sulfuric acid thereto. And then the solution was washed with sodium bicarbonate water solution and extracted with ethyl acetate. The collected ethyl acetate layer was concentrated by removing organic solvent and remaining residue was purified by column chromatography to isolate 32 mg of pheophorbide α triethylene glycol methyl ester (8):

$^1$H-NMR (500 MHz, CDCl$_3$) δ: 9.53 (s, 1 H, meso-H), 9.40 (s, 1H, meso-H), 8.57 (s, 1H, meso-H), 8.00 (dd, 1H, J=6.4, 11.5 Hz, CH$_2$=CH), 6.30 (d, 1H, J=17.9 Hz, CH=CH$_2$), 6.29 (d, 1H, CH), 6.19 (d, 1H, J=12.5 Hz, CH=CH$_2$), 4.49–4.44 (m, 3H, CH and OCH$_2$), 4.26–4.24

(m, 1H, CH), 4.15–4.07 (m, 2H, OCH$_2$), 3.74–3.65 (m, 4H, CH$_2$ and OCH$_2$), 3.69 (s, 3H, OCH$_3$), 3.58–3.43 (m, 14H, OCH$_2$), 3.41 (s, 3H, CH$_3$), 3.35 (t, 2H, J=4.5 Hz, CH$_2$), 3.30–3.28 (m, 2H, CH$_2$), 3.24 (s, 3H, CH$_3$), 2.66–2.02 (m, 6H, CH$_2$CH$_2$ and OH), 1.82 (d, 3H, J=7.3 Hz, CH$_3$), 1.70 (t, 3H, J=7.6 Hz, CH$_3$), 0.55 (br. s., 1H, N—H), −1.62 (br. s., 1H, N—H).

Example 8

Preparation of Methyl Pheophorbide a Diethyleneglycol Ester (9)

A solution of pheophytin α (60 mg) was dissolved in small amount of dichloromethane. 20 ml of diethyleneglycol and 1 ml of sulfuric acid were added thereto and stirred for 23 hrs. And then the solution was washed with saturated sodium bicarbonate water solution and extracted with chloroform. The collected chloroform layer was concentrated by removing organic solvent and remaining residue was purified by column chromatography to isolate 2 mg of methyl pheophorbide α diethylene glycol ester (9):

$^1$H-NMR (500 MHz, CDCl$_3$) δ: 9.26 (s, 1 H, meso-H), 8.34 (s, 1H, meso-H), 7.92 (dd, 1H, J=6.0, 11.8 Hz, CH$_2$=CH), 6.33 (s, 1H, OH), 6.25 (d, 1H, J=17.8 Hz, CH=CH$_2$), 6.17 (d, 1H, J=11.6 Hz, CH=CH$_2$), 4.88 (br. s, 2H. OH), 4.76–4.60 (m, 4H, CH$_2$ CH$_2$), 4.41–4.33 (m, 3H, CH and CH$_2$), 4.27–4.23 (m, 2H, CH and OCH$_2$), 3.96–3.94 (m, 2H, CH$_2$), 3.88–3.80 (m, 6H, CH$_2$), 3.75 (s, 3H, OCH$_3$), 3.75–3.69 (m, 2H, CH$_2$), 3.58 (s, 3H, CH$_3$), 3.31 (s, 3H, CH$_3$), 3.18 (s, 3H, CH$_3$), 2.75–2.00 (m, 4H, CH$_2$CH$_2$), 2.03 (d, 3H, J=7.0 Hz, CH$_3$), 1.64 (t, 3H, J=7.3 Hz, CH$_3$), 0.87 (br. s., 1H, N—H), −1.85 (br.s., 1H, N—H).

Example 9

Preparation of Methyl Pheophorbide a Triethyleneglycol Ester (10)

A solution of methyl pheophorbide α methyl ester (100 mg) dissolved in 16 ml of pyridine was added to 15 ml of toluene. 0.033 ml of triethyleneglycol was added thereto and heated for 16 hrs at nitrogen gas atmosphere. And then the solution was extracted with methylene chloride. The collected methylene chloride layer was concentrated by removing organic solvent and remaining residue was purified by column chromatography to isolate 73 mg of methyl pheophorbide α triethylene glycol ester (10) designated as DH-1-180-3 hereinafter:

UV spectrum: See FIG. 1

H-NMR (500 MHz, CDCl$_3$) δ: 9.53 (s, 1 H, meso-H), 9.40 (s, 1H, meso-H), 8.57 (s, 1H, meso-H), 8.00 (dd, 1H, J=6.3, 11.5 Hz, CH$_2$=CH), 6.30 (d, 1H, J=18.1 Hz, CH=CH$_2$), 6.27 (s, 1H. CH), 6.19 (d, 1H, J=12.8 Hz, CH=CH$_2$), 4.49–4.45 (m, 3H, CH and OCH$_2$), 4.26–4.24 (m, 1H, CH), 3.72–3.66 (m, 4H, CH$_2$ and CH$_2$), 3.69 (s, 3H, OCH$_3$), 3.55 (s, 3H, OCH$_3$), 3.49–3.39 (m, 4H, CH$_2$OCH$_2$), 3.41 (s, 3H, CH$_3$), 3.31 (t, 2H, J=4.6 Hz, CH$_2$), 3.26–3.23 (m, 5H, CH$_2$ and CH$_3$), 2.66–2.21 (m, 5H, CH$_2$CH$_2$ and OH), 1.82 (d, 3H, J=7.3 Hz, CH$_3$), 1.70 (t, 3H, J=7.6 Hz, CH$_3$), 0.54 (br. s., 1H, N—H), −1.62 (br. s., 1H, N—H).

Experimental Example 1

Determination of Transforming Activity of Present Compounds into Singlet Oxygen State The transforming activity of the target compounds into singlet oxygen state was measured by following methods.

Methods

The experimental assay was performed under air-saturated condition (99.999% ultra-purified gas) using toluene (Merck Co. HPLC grade) as a solvent, in the oxygen concentration in the solution of $2.1 \times 10^{-3}$ M at 21° C.

Result

Figure 2:
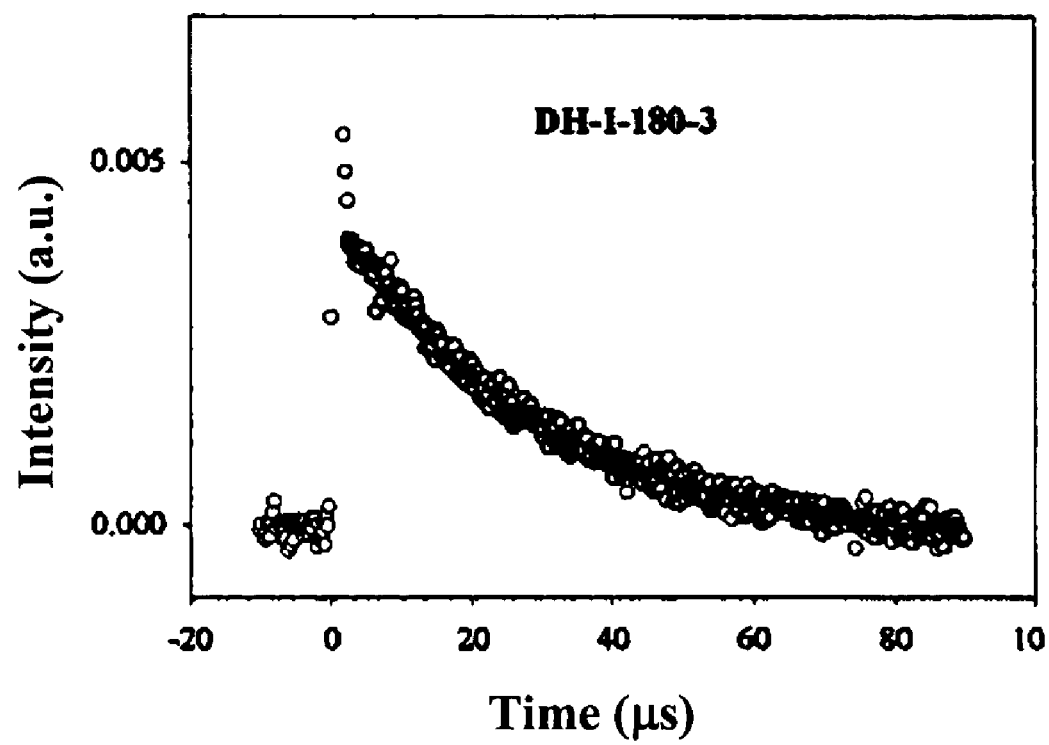
FIG. 2 shows the result of determination of singlet oxygen state at 508 nm (λ excitation)
Figure 2:
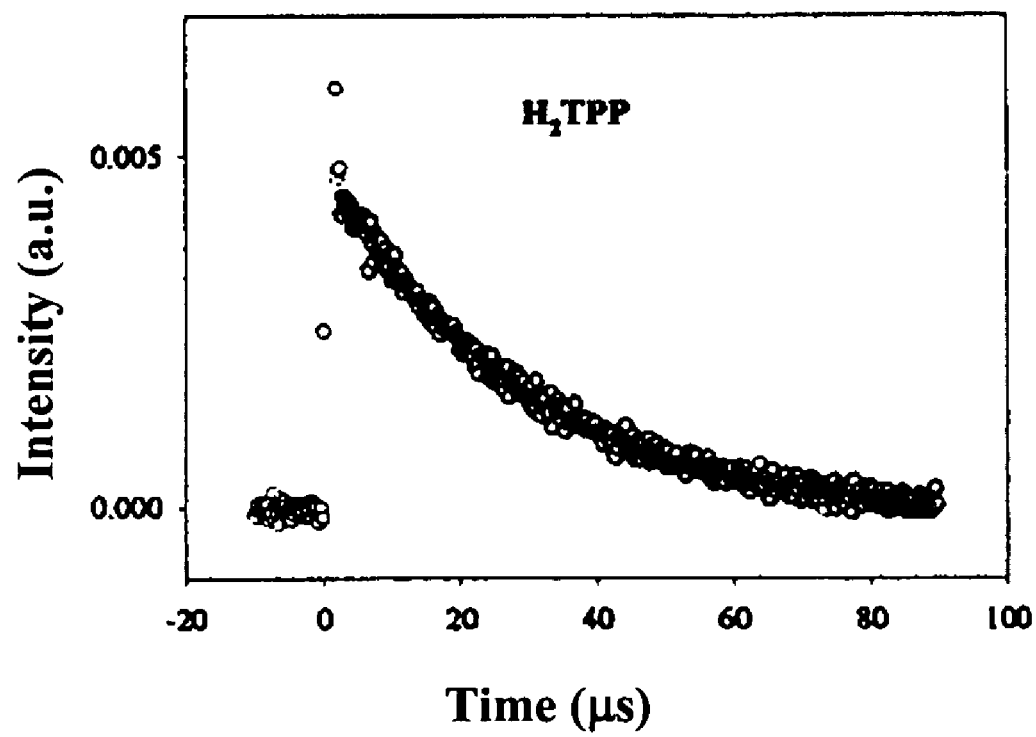

At the result of determination of singlet oxygen state at 508 nm (λexcitation), the transformed photon yield was 0.60 (5%) as can be seen in FIG. 2. Therefore, it is confirmed that the transforming activity of DH-1-180-3 into singlet oxygen state is excellent and the physical stability thereof is also good.

Experimental Example 2

Determination of Anticancer Activity of Present Compounds

The anticancer activity of the target compounds was determined by following experiments.

In Vivo Assay

DH-1-180-3 as a test sample of the present invention and photofrin (photogem®) as a control group were used in test.

Breast cancer cell line (EMT6; $1 \times 10^6$ cells/mouse) was transplanted to BALB/c mouse (12 per group) and 7 to 10 days later, test sample diluted with 1% Tween 80 and control drug diluted with injection water were administrated to each mouse at the dose of 0.4 and 0.8 mg/kg/mouse in test sample group and 2 mg/kg/mouse in control group respectively.

Three hours later, the mice were anesthetized and irradiation was subjected thereto at the strength of 1.2 J using by halogen lamp. The tumor size of each mice was determined using by caliper at the interval of 2 or 3 days and the survival ratio of the mice according to tumor was also determined.

In Vitro Assay

Breast cancer cell line (EMT6; $1 \times 10^6$ cells/mouse) was cultured in culture medium (DMEM+10% FBS+100 units of Penicillin+100 μg streptomycin), treated with 0.25% Trypsin-EDTA to collect the cells and the number of cells was counted using by Trypan blue staining reagent.

Each 3 ml of cells was added to 35 mm of culture dish in the concentration of $2 \times 10^5$ cells/ml and incubated in 5% CO$_2$ incubator for 24 hrs in order that the cells be arranged to be made a mono-layer.

Various concentrations of DH-1-180-3 dissolved in DMF were added to 35 mm of culture dish adjusting the concentration of DMF solvent not to exceed 0.5% to exclude the effect of DMF. Photosensitizing substance was added thereto and irradiation was subjected thereon at the strength of 1.2 J using by halogen lamp. The culture dishes were transferred to incubators and incubated.

The cell cytotoxicity caused by PDT was analyzed by MTT assay and the morphology of cells was observed by microscopy.

Conventional photosensitizer, i.e., photogem®, was used as a comparative control group and several factors such as the concentration of test samples, the irradiation strength of light and the absorption time of samples etc were modified in the present experiment.

Result

Figure 3:
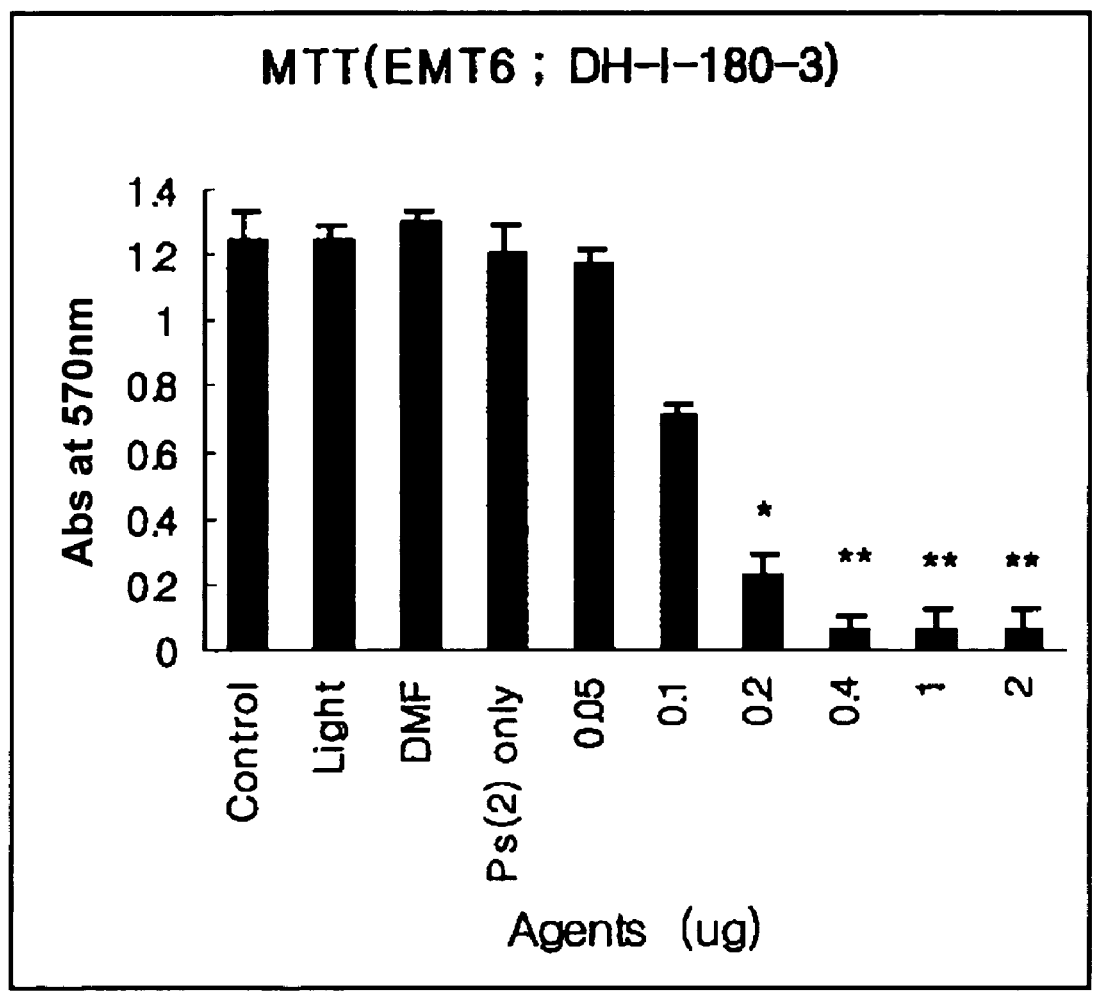
FIG. 3 represents the result of cell cytotoxicity on mouse EMT6 cell line determined by MTT assay, of which control group (control), light only irradiation group (light), the group treated with solvent (DMF), the group treated with photosensitizer samples without light (Ps(2) only) and the group treated with present photosensitizing substance (DH-1-180-3) denote respectively.

FIG. 3 represents the result of cell cytotoxicity on mouse EMT6 cell line determined by MTT assay.

As can be seen in FIG. 3, while the groups including light only irradiating group (light), the group treated with DMF only (DMF), the group treated with photosensitizer sample without light (PS(2) only) do not show cell cytotoxicty, the photosensitizer treated groups, in particular, the group treated with 0.2 μg of photosensitizer of the present invention shows remarkable cytotoxicity and $LD_{100}$ of the test group was shown in 0.4 μg of photosensitizer treated group, which is a most effective concentration.

Figure 4:
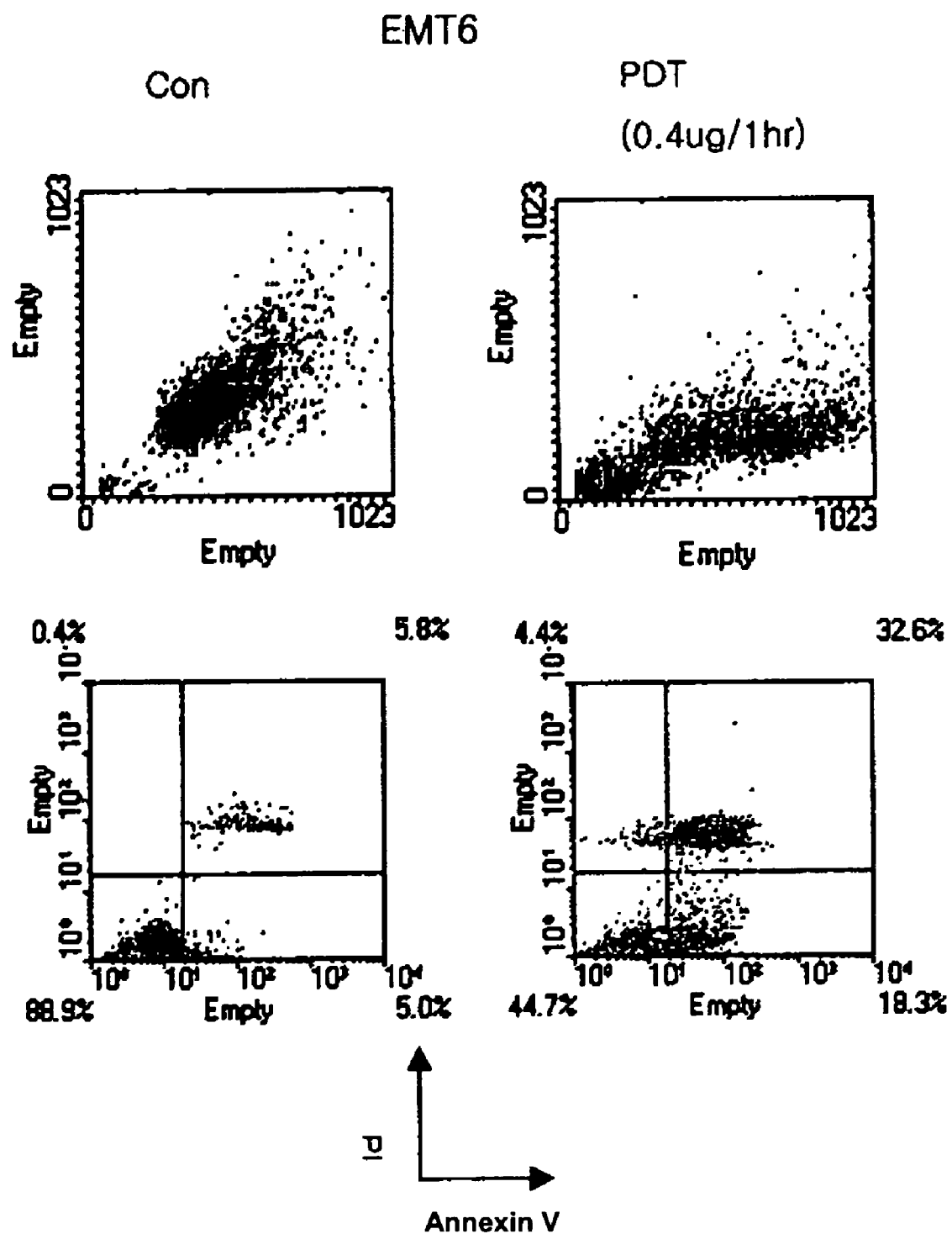
FIG. 4 presents the staining result with Annexin V/PI staining to study the mechanism of cell apoptosis.

FIG. 4 presents the staining result with Annexin V/PI staining to study the action mechanism of cell apoptosis.

As can be seen in FIG. 4, while above 90% of cells survived in control group, more than 50 to 60% of cells were dead in PDT treatment group (0.2 μg/hr), which shows that EMT6 cells were dying from cell apoptosis.

Figure 5:
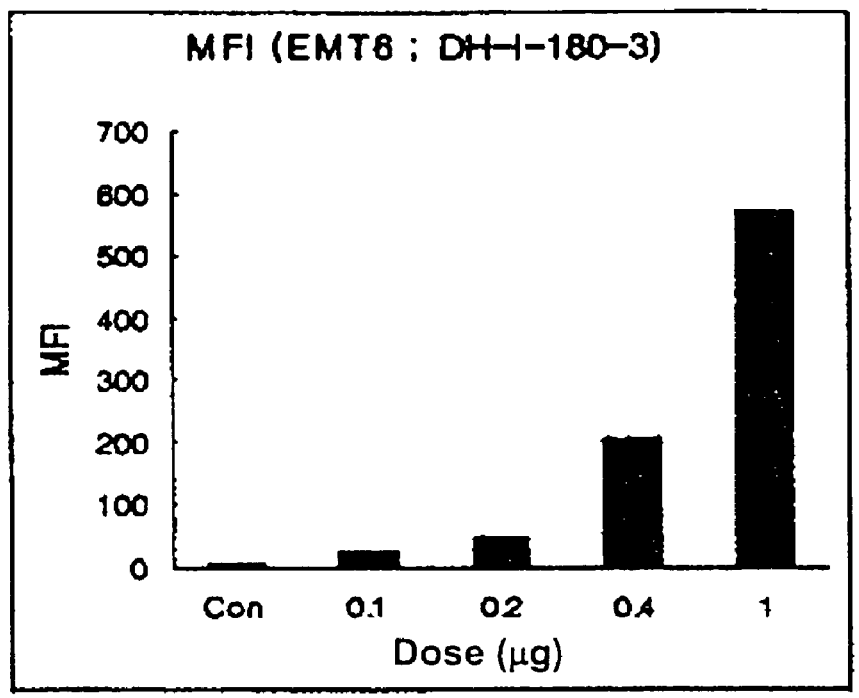
FIG. 5 presents the diagram determining the uptake amount of PDT within cells according to various concentrations of PDT through FACS analysis.
Figure 5:
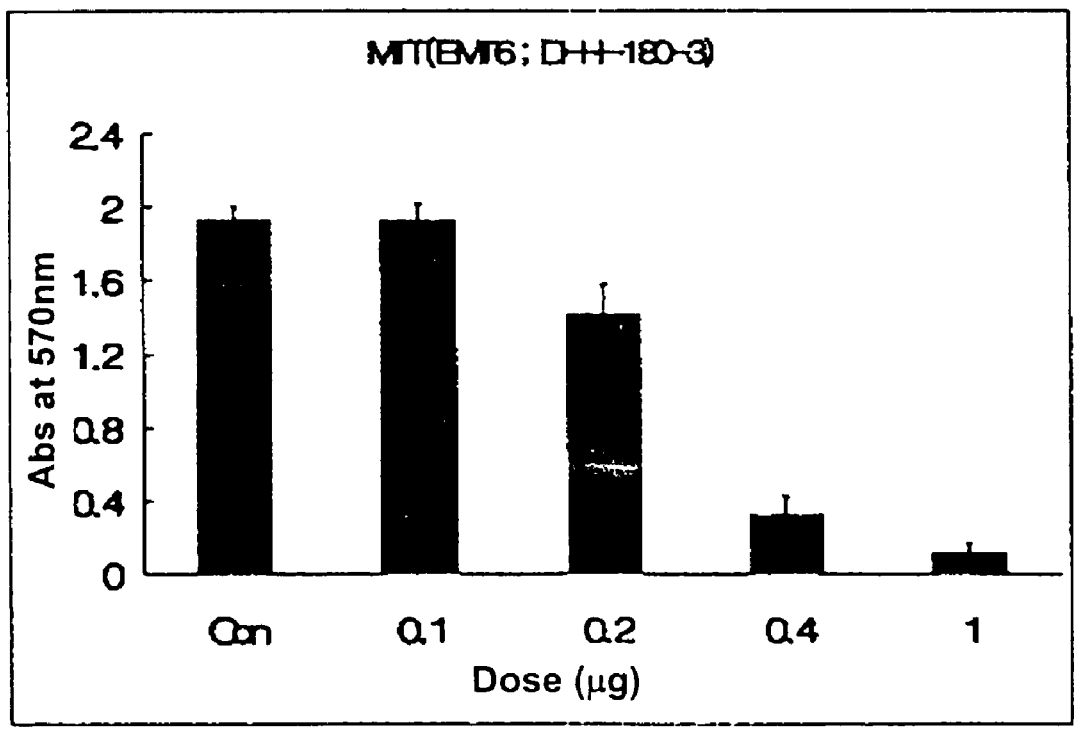

FIG. 5 presents the diagram determining the uptake amount of PDT within the cells according to various concentrations of PDT through FACS analysis.

As can be seen in FIG. 5, the uptake amount of PDT within cells was increased with the concentrations of PDT in a dose dependent manner and is deeply correlated with cell cytotoxicity. It is confirmed that the strongest cell cytotoxicity was shown where the value of MFI (Mean Fluorescence Intensity) is 208.92, i.e., and where the concentration of DH-I-180-3 is at least 0.4 μg.

Figure 6:
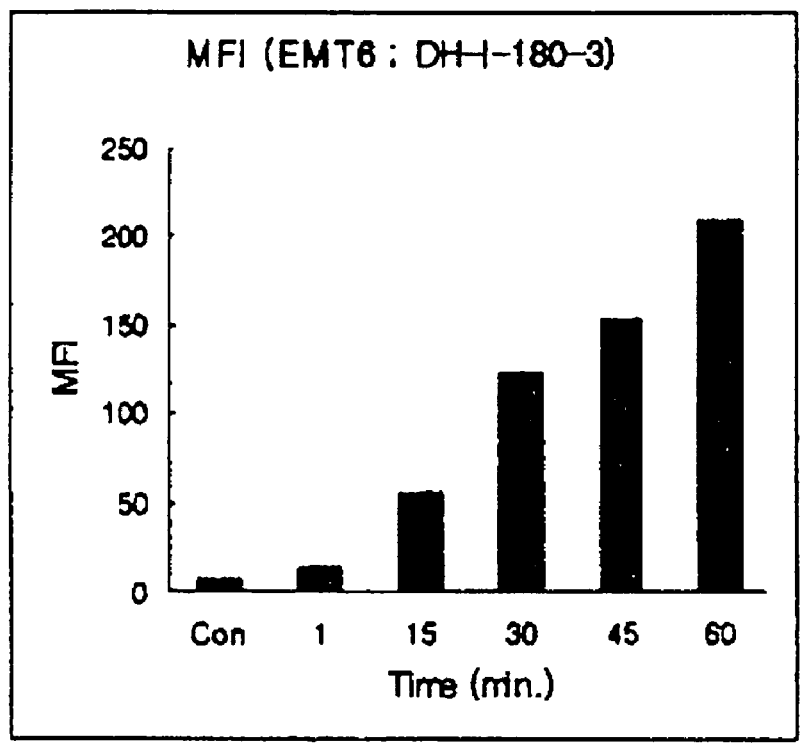
FIG. 6 presents the diagram determining the accumulation ratio of PDT in cell according to duration time through FACS analysis.
Figure 6:
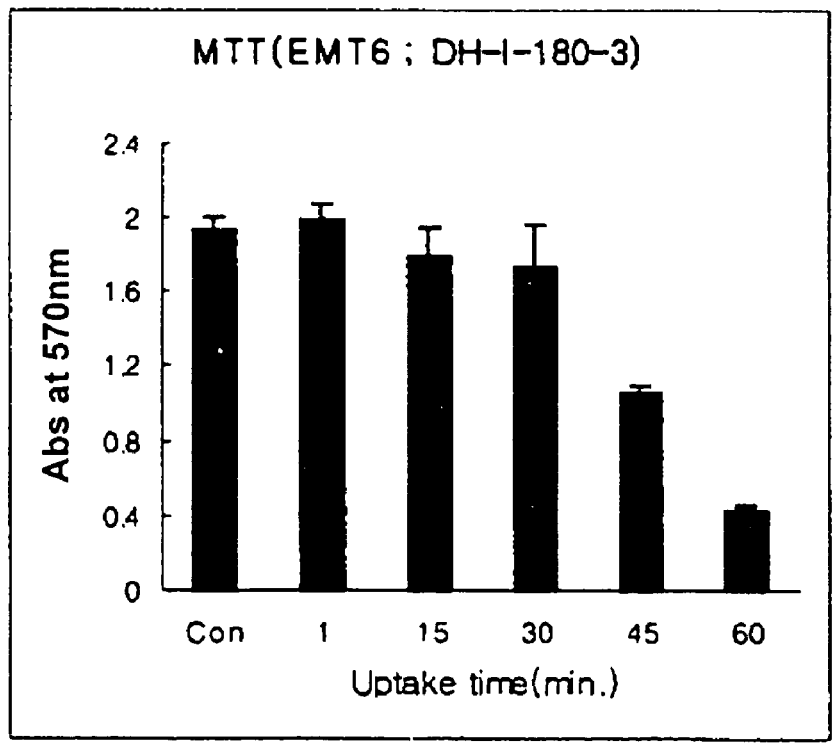

FIG. 6 presents the diagram determining the accumulation ratio of PDT in cells according to the duration time through FACS analysis.

As can be seen in FIG. 6, the accumulation ratio of PDT within cells was increased with the duration time and is deeply correlated with cell cytotoxicity. It is confirmed that the strongest cell cytotoxicity was shown where the value of MFI (Mean Fluorescence Intensity) is reached at 208.92, i.e., and where the duration time is at least 60 minutes.

Figure 7:
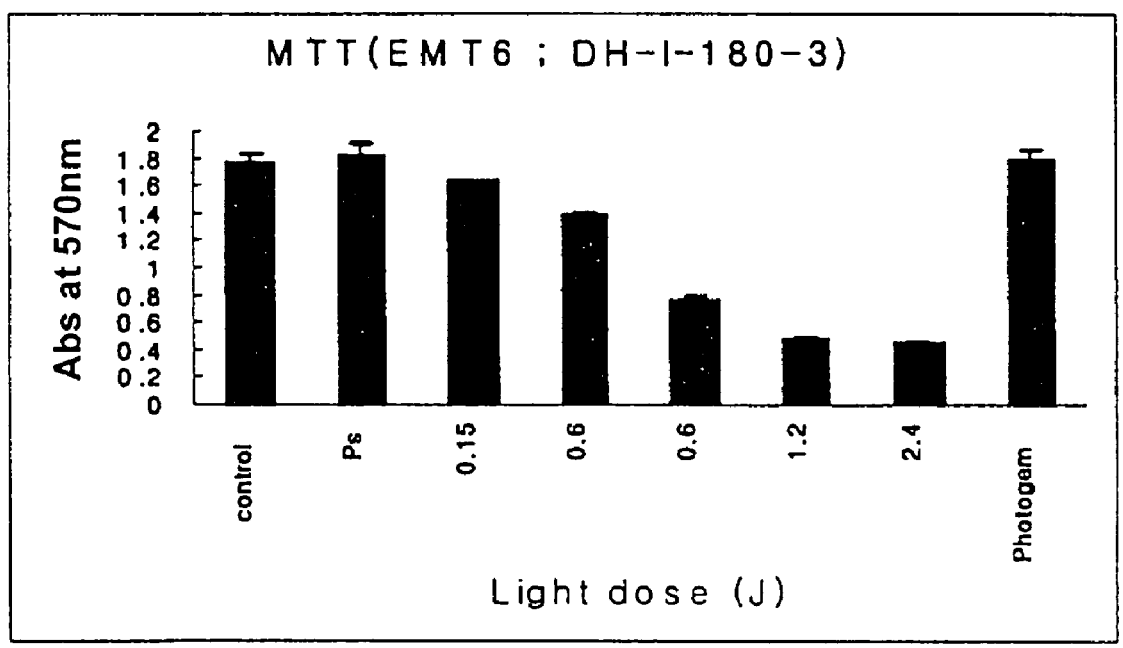
FIG. 7 presents the diagram determining the degree of cell cytotoxicity according to the intensity of irradiating light.

FIG. 7 presents the diagram determining the degree of cell cytotoxicity according to the intensity of irradiating light.

As can be seen in FIG. 7, it is confirmed that the strongest cell cytotoxicity was shown where the intensity of irradiating light is reached at 1.2 J, but no more effective over the intensity.

Figure 8:
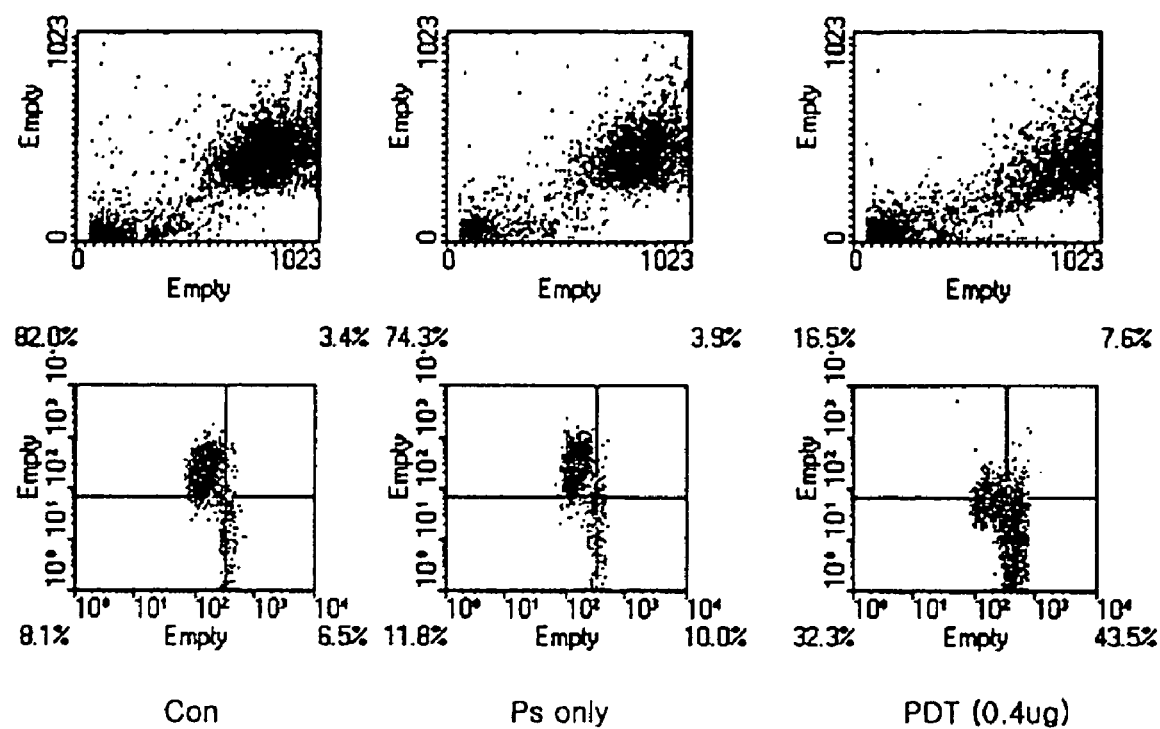
FIG. 8 depicts the diagram determining MMP (mitochondrial membrane potential) within EMT6 cell after the treatment of PDT and JC-1 dye staining by FACS analysis.

FIG. 8 depicts the diagram determining MMP (mitochondrial membrane potential) within EMT6 cell after the treatment of PDT and JC-1 dye staining by FACS analysis.

As can be seen in FIG. 8, it is confirmed that MMP is remarkably decreased with PDT, which is consistent with the observation result with fluorescence microscopy.

Figure 9:
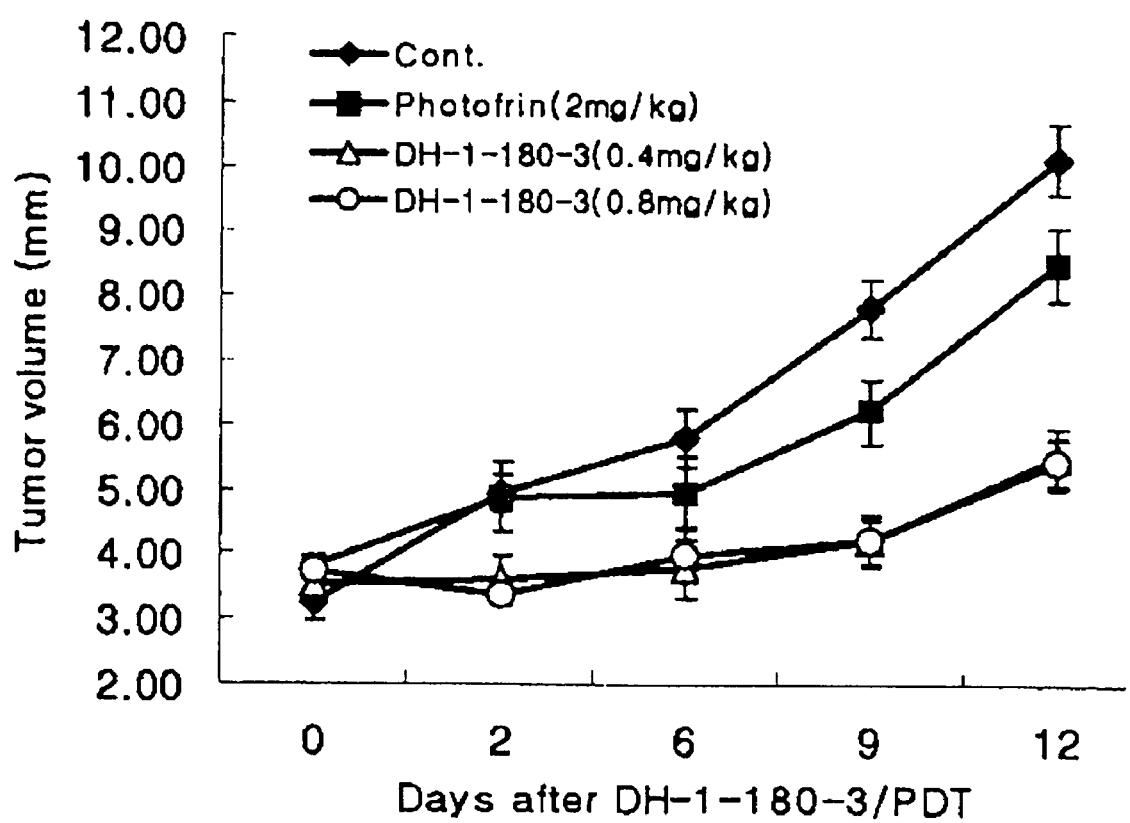
FIG. 9 depicts the inhibition of tumor of BALB/c mouse caused by DH-1-180-3 treated EMT6 cell.

FIG. 9 depicts the inhibition of tumor of BALB/c mouse caused by DH-1-180-3 treated EMT6 cell.

As can be seen in FIG. 9, it is confirmed that the growing ratio of tumor in PDT treated group was remarkably decreased with the treatment time comparing with those in control group and photofrin (photogem®) treated group.

Figure 10:
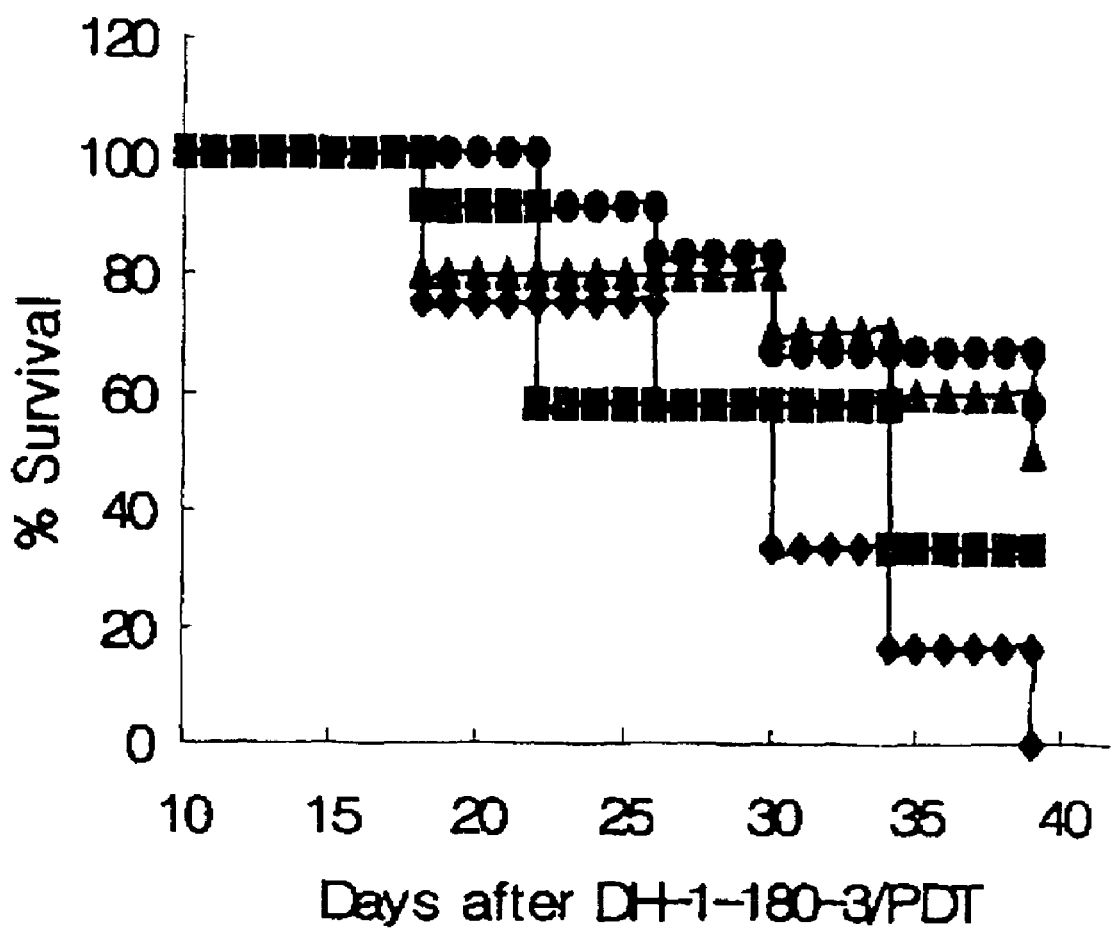
FIG. 10 depicts the survival curve obtained by the result of FIG. 9.

FIG. 10 depicts the survival curve obtained by the result of FIG. 9.

As can be seen in FIG. 10, it is confirmed that the survival ratio in PDT treatment group was extended comparing with that in control group.

Based on the aforementioned test results, it is an optimum condition to treating DH-1-180-3 of the present invention in condition that the concentration of photosensitizer used in PDT is 0.4 μg/ml, the optimum absorption time is 1 hour, the irradiation intensity is 1.2 J and the analysis time for determining its activity is 24 hrs. However, photofrin (photogem®)) could not effective at the concentration ranging 50–100 μg/ml, in 24 hours and its intensity of irradiation light is required to fulfill the same effect is above 10 to 100 folds that of DH-1-180-3.

Experimental Example 3

Toxicity Test

Methods

The acute toxicity tests on ICR mice (mean body weight 25±5 g) and Sprague-Dawley rats (235±10 g) were performed using the compounds 1 and 10. Each group consisting of 3 mice or rats was administrated intraperitoneally with 20 mg/kg, 10 mg/kg and 1 mg/kg of test compounds or solvents (0.2 ml, i.p.), respectively and observed for 24 hrs.

Results

There were no treatment-related effects on mortality, clinical signs, body weight changes and gross findings in any group or either gender. These results suggested that the compounds prepared in the present invention were potent and safe.

Hereinafter, the formulating methods and kinds of excipients will be described, but the present invention is not limited to them. The representative preparation examples were described as follows.

| Preparation of powder | |
| --- | --- |
| Compound 10 | 500 mg |
| Corn Starch | 100 mg |
| Lactose | 100 mg |
| Talc | 10 mg |

Powder preparation was prepared by mixing above components and filling sealed package.

| Preparation of tablet | |
| --- | --- |
| Compound 10 | 100 mg |
| Corn Starch | 100 mg |
| Lactose | 100 mg |
| Magnesium Stearate | 2 mg |

Tablet preparation was prepared by mixing above components and entabletting.

| Preparation of capsule | |
| --- | --- |
| Compound 1 | 50 mg |
| Lactose | 50 mg |
| Magnesium Stearate | 1 mg |

Tablet preparation was prepared by mixing above components and filling gelatin capsule by conventional gelatin preparation method.

| Preparation of injection | |
| --- | --- |
| Compound 1 | 100 mg |
| Distilled water for injection | optimum amount |
| PH controller | optimum amount |

Injection preparation was prepared by dissolving active component, controlling pH to about 7.5 and then filling all the components in 2 ml ample and sterilizing by conventional injection preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The compounds according to the present invention are useful in the prevention, or treatment of various cancer diseases and have superior advantages such as excellent photon yield to produce singlet oxygen, good physical stability and potent cell cytotoxicity to conventional photosensitizers.

What is claimed is:

1. A compound represented by the following formula (II), and the pharmaceutically acceptable salt thereof:

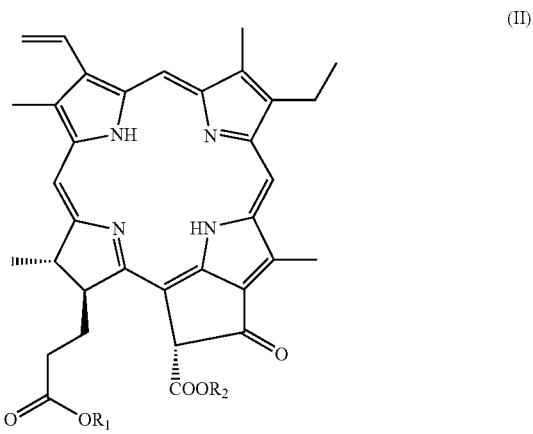

wherein
$R_1$ is a straight or branched lower alkyl or alkoxy group having 1–6 carbon atoms, an ethylene glycol group of formula $-(OCH_2CH_2O)_n-$ where n=4, 6 or 7, an ethylene glicol group, a diethylene glycol group, a triethylene glycol group or a methoxyethylene glycol group; and
$R_2$ is an ethylene glycol group of formula $-(OCH_2CH_2O)_n-$ where n=4, 6 or 7, is an ethylene glycol group, which can chelate with transition metal ions comprising Ni metal ion.

2. A pharmaceutical composition comprising the compound of formula (II) as set forth in claim 1 pharmaceutically acceptable Salt thereof as an active ingredient together with a pharmaceutically acceptable carrier to treat breast cancer by way of reproducing singlet state oxygen radical.

3. A method of treating breast cancer in human or mammal, wherein the method comprises administering a therapeutically effective amount of the compound of formula of (II) as set forth in claim 1 or pharmaceutically acceptable salt thereof.

* * * * *

UNITED STATES PATENT AND TRADEMARK OFFICE
CERTIFICATE OF CORRECTION

PATENT NO. : 7,019,132 B2
APPLICATION NO. : 10/718734
DATED : March 28, 2006
INVENTOR(S) : Woo et al.

It is certified that error appears in the above-identified patent and that said Letters Patent is hereby corrected as shown below:

On Title Page

Column 1, please change Item (73) Assignee from "Kostarworld Co., Ltd." to -- Technomart Co., Ltd. --

Signed and Sealed this

Sixteenth Day of October, 2007

JON W. DUDAS
*Director of the United States Patent and Trademark Office*